United States Patent [19]
LeMaire, III et al.

[11] Patent Number: 5,989,277
[45] Date of Patent: Nov. 23, 1999

[54] SURGICAL INSTRUMENT WITH OFFSET JAW ACTUATOR

[76] Inventors: Norman J. LeMaire, III, 595 Pleasant St., Raynham, Mass. 02767; William R. Hanna, Jr., 5500 N. Main St. Bldg. 15 Apt. 209, Fall River, Mass. 02720

[21] Appl. No.: 09/016,090

[22] Filed: Jan. 30, 1998

[51] Int. Cl.⁶ .................................................. A61B 17/32
[52] U.S. Cl. .................... 606/170; 606/205; 606/207; 74/579 R
[58] Field of Search ................ 606/170, 83, 174, 606/173, 177, 172, 208, 207, 205, 206; 74/579 R; 403/91; 604/22

[56] References Cited

U.S. PATENT DOCUMENTS

| | | | |
|---|---|---|---|
| 4,712,545 | 12/1987 | Honkanen | 128/305 |
| 5,152,780 | 10/1992 | Honkanen et al. | 606/205 |
| 5,219,357 | 6/1993 | Honkanen et al. | 606/205 |
| 5,366,477 | 11/1994 | LeMaire et al. | 606/208 |
| 5,389,104 | 2/1995 | Hahnen et al. | 606/174 |
| 5,395,375 | 3/1995 | Turkel et al. | 606/83 |
| 5,443,475 | 8/1995 | Auerbach et al. | 606/170 |
| 5,571,131 | 11/1996 | Ek et al. | 606/184 |
| 5,590,570 | 1/1997 | LeMaire et al. | 74/579 R |
| 5,603,724 | 2/1997 | O'Connor | 606/207 |
| 5,649,947 | 7/1997 | Auerbach et al. | 606/170 |

*Primary Examiner*—Michael Buiz
*Assistant Examiner*—Lien Ngo
*Attorney, Agent, or Firm*—Ronald R. Kilponen

[57] ABSTRACT

A tool for grasping or cutting with an offset jaw actuator is shown. The offset provides a consistent width to the actuator discouraging buckling under heavy loading situations. The offset also provides for greater contact area between the actuator and inner tip. The interface of the actuator with the inner tip is machined into the inner tip from the side resulting in an instrument that is easier and cheaper to manufacture and clean while retaining maximum strength for cutting or grasping.

12 Claims, 11 Drawing Sheets

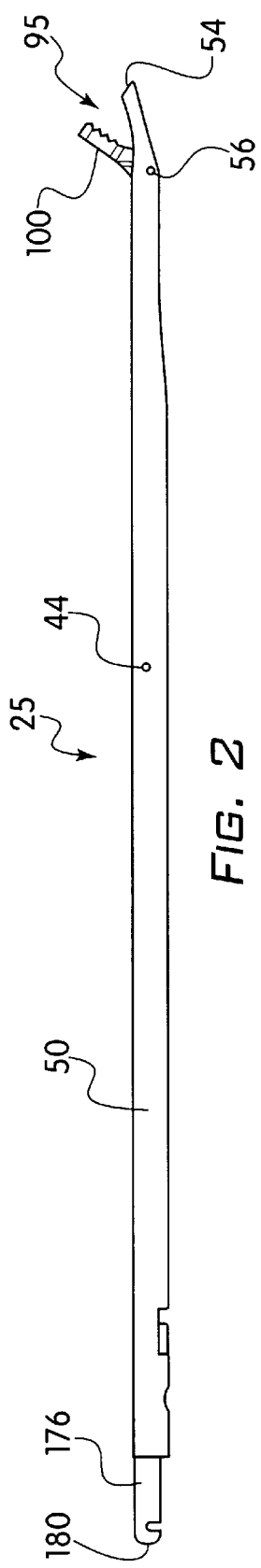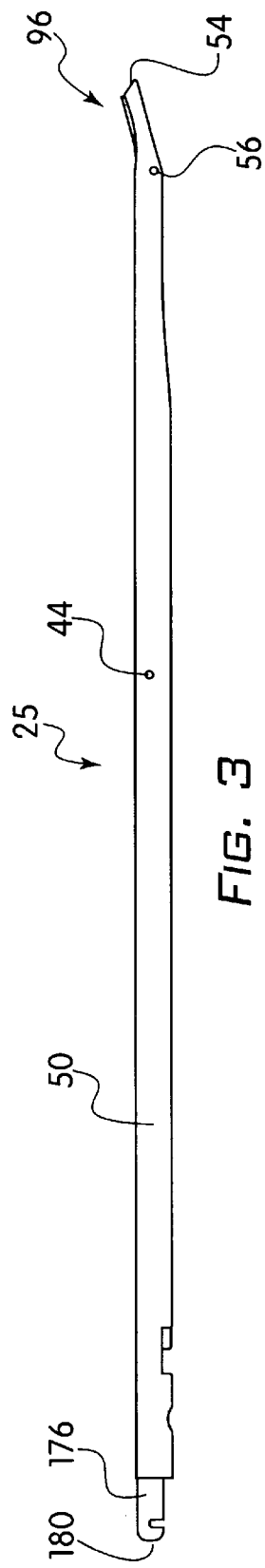

SURGICAL INSTRUMENT WITH OFFSET JAW ACTUATOR

FIELD

The present version of this invention relates generally to the field of surgical instruments utilized primarily in non-invasive surgery. Other uses of the principles of this instrument may find application in industries or professions requiring the use of grasping or cutting tools.

BACKGROUND

Surgical punches and graspers have been know in the art for some time. They generally involve a fixed or stationary member, an actuator extending from an actuator handle to the working end of the stationary member where the actuator engages a jaw member.

Actuation of the actuator causes the jaw member to pivot and open relative to the stationary member where tissue is inserted between the jaw member and die portion of the stationary member. The handle is then operated to close the jaw member relative to the stationary member where the engaged tissue is lacerated or grasped and can then be removed.

This type of operation is well known in the art and various types of surgical instruments have been developed. This process however puts large stresses on the components of the instruments due to the high forces needed to lacerate or grasp and remove some tissue. These high stresses cause premature failure of the instruments from wear or worse yet catastrophic failure of the components while in use, resulting in metal fragments or slivers being dispersed in the operative site. The metal fragments are often difficult to locate and remove causing unnecessary complications, increased medical time and greater possibility of less than optimum patient results. If metal fragments or slivers remain from catastrophic instrument failure and are not located and removed after the failure, a second procedure may be necessary to remove the metal fragments or slivers and to correct or rectify any tissue damage that may have occurred.

A typical failure mode in the prior art occurred when the pin attaching the jaw member to the stationary member or the pin attaching the actuator to the jaw member failed. Other failures occurred when the actuator bar was forced such that the bar bent, essentially locking the instrument. A jammed actuator bar would sometimes fail with the jaw member in a fully opened position and this would then cause damage to the operative site when removing the instrument with the jaw locked open. Another typical failure occurred when closing the jaw member on a piece of hard tissue, the actuator bar would fail and buckle upward immediately before the connection of the actuator bar and the jaw member. This was due to the necking down of the height and width of the actuator bar. Still other failures occurred when the contact surfaces between the actuator bar and the inner tip fractured and jammed the instrument.

Several other embodiments have addressed these problems by eliminating the pins typically used to attach the jaw member to the actuator and the jaw member to the stationary member. The pins have been replaced by a lug and groove arrangement. This procedure is costly and difficult to machine due to the precise dimensions required for smooth non-binding operation and the small size of the components.

Several other embodiments have utilized a pin for one of the attachments, either between the jaw member and actuator or between the jaw member and stationary member with a lug and groove for the other attachment. These prior art embodiments still had failures of the lug and groove surfaces due to high loading and small contact surfaces. These embodiments have tried to decrease the likelihood of catastrophic failure or premature failure by increasing the size of the components and attachments resulting in larger instrument size and more damage to the operative site from the increased size of the incisions and instruments. Large instrument size also decreases the finesse that can be obtained in the operation of the instruments in removing only specific tissue, resulting in removal of more tissue than may be necessary and therefore longer healing time and less than optimum patient results and recovery.

Consequently there is a need for an instrument in which the size can be kept at a minimum while the cutting force applied to the components can be kept high resulting in the minimizing of the likelihood of catastrophic failure or premature wear from overloading. The instrument should have a high strength to size ratio and have an optimum design to allow the highest operational forces for the smallest size with the appropriate materials.

SUMMARY

In view of the foregoing disadvantages well known in the prior art there is a need for a surgical instrument with an offset jaw actuator.

A first object of this embodiment of the invention is to provide a relatively easy design to manufacture.

A second object of this embodiment of the invention is to provide an instrument having a small size.

Another object of this embodiment of the invention is to provide an instrument capable of operating with high actuation forces while minimizing the likelihood of instrument failure.

An additional object of this embodiment of the invention is to provide an instrument having both a small size and capable of handling high actuation forces while minimizing the likelihood of instrument failure.

Another object of this embodiment of the invention is to provide an instrument with an increased life expectancy from decreased wear thereby requiring less maintenance and less cost over the lifetime of the instrument.

An additional object of this embodiment of the invention is to provide an instrument having enough strength to decrease the probability of catastrophic failure of components.

Another object of this embodiment of the invention is to provide an instrument capable of use in small work areas.

Another object of this embodiment of the invention is to provide an instrument that is more easily flushed and cleaned following use.

These together with other objects of this instrument, along with various features of novelty which characterize this instrument, are pointed out with particularity in the claims annexed hereto and forming a part of this disclosure. For a better understanding of this instrument, its operating advantages and the specific objects attained by its uses, reference should be had to the accompanying drawings and following descriptive matter in which there is illustrated a preferred embodiment of this version of the instrument.

BRIEF DESCRIPTION OF DRAWINGS

FIG. 2 shows a side view of the instrument with the inner tip in the open or second position.

FIG. 3 shows a side view of the instrument with the inner tip in the closed or first position.

DETAILED DESCRIPTION OF THE PREFERRED EMBODIMENTS

Figure 1:
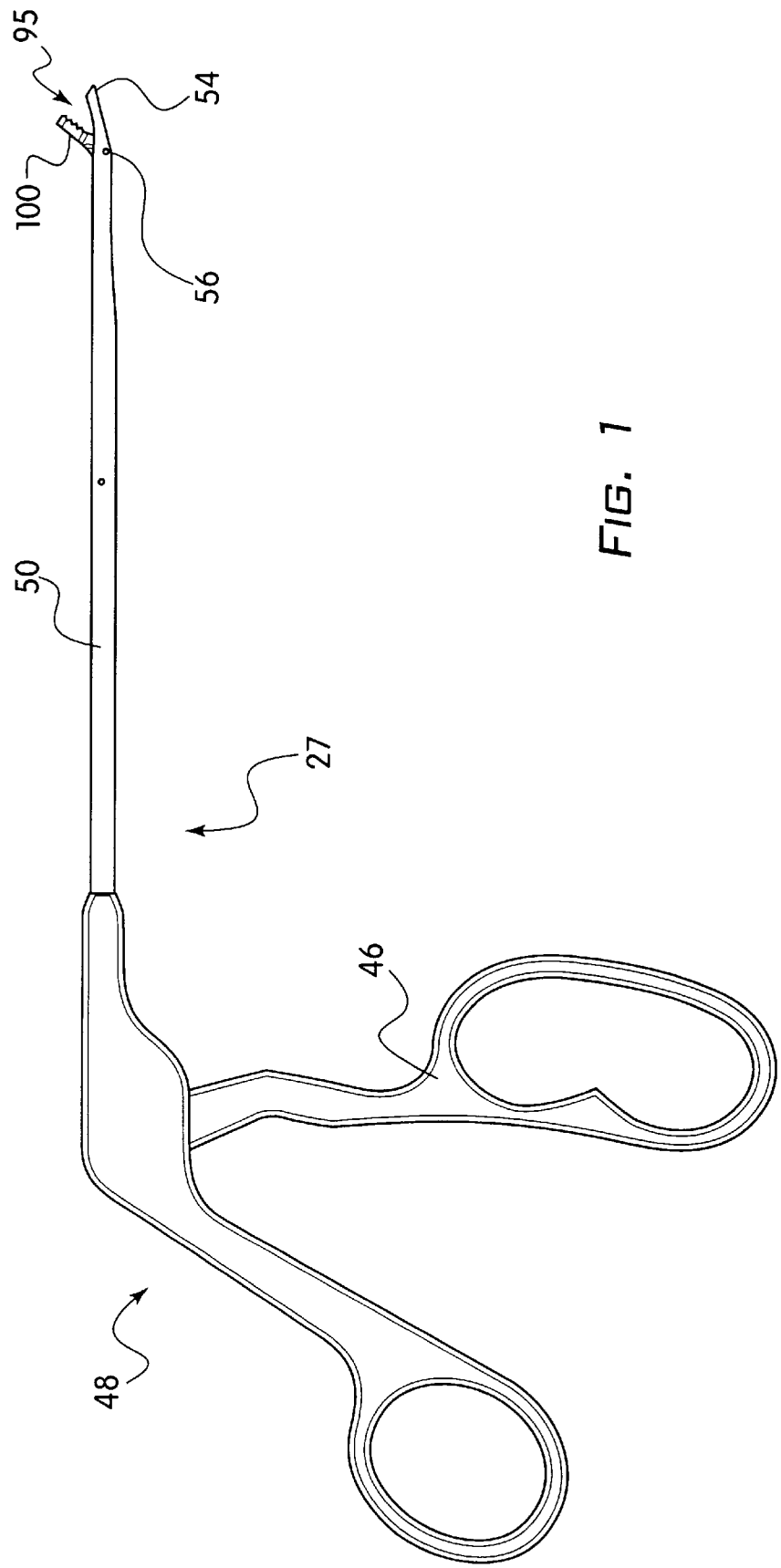
FIG. 1 shows a side view of the surgical tool with one embodiment of the hand grip.
Figure 4:
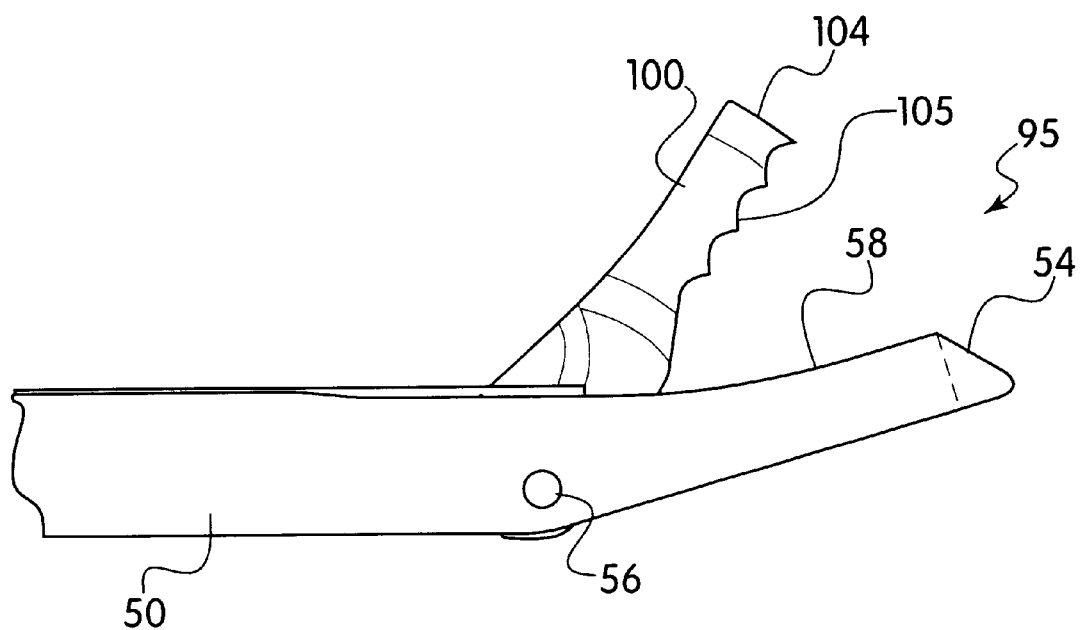
FIG. 4 shows a detail partial side view of the closed end with the inner tip in the open or second position.
Figure 5:
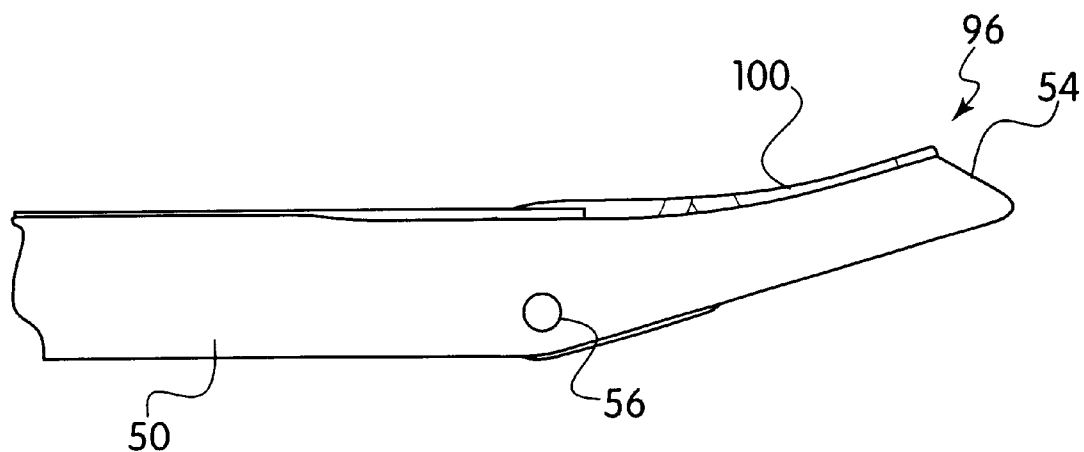
FIG. 5 shows a detail partial side view of the closed end with the inner tip in the closed or first position.

Referring to the drawings in detail wherein like elements are indicated by like numerals, there is shown in FIG. 1 the surgical tool 27 having a hand grip 48 connected to an outer shaft 50. FIG. 2 shows a view of the instrument 25 in the open position 95, or where the inner tip 100 is in a position farthest away from the outer shaft 50 and the actuator bar 176 actuation end 180 is farthest from the outer shaft 50. FIG. 3 shows the instrument 25 in the closed position 96, where the inner tip 100 is contained primarily within the closed end 54 of outer shaft 50 and the actuator bar 176 actuation end 180 is closest to the outer shaft 50. Other means for translating the actuation bar 176 could include threads, triggers, ratchets, electrical motors and others providing a translational movement to the actuator bar 176. This disclosure is not meant to limit these means only to the hand grip 48 as shown.

The inner tip 100, outer shaft 50, and actuator bar 176 are, in a preferred embodiment, machined from stainless steel. Other materials, both ferrous and non-ferrous could be substituted.

Figure 6:
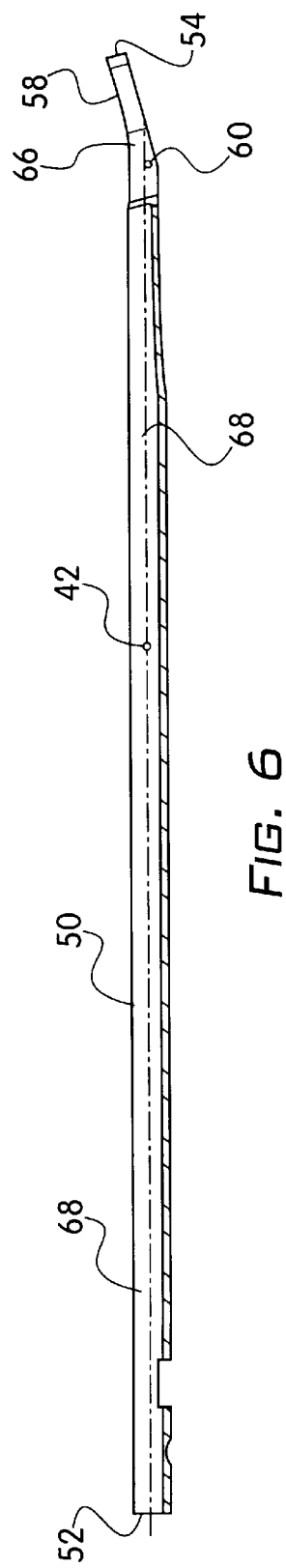
FIG. 6 shows a cross section view along longitudinal axis A—A in FIG. 16, of the outer shaft.
Figure 8:
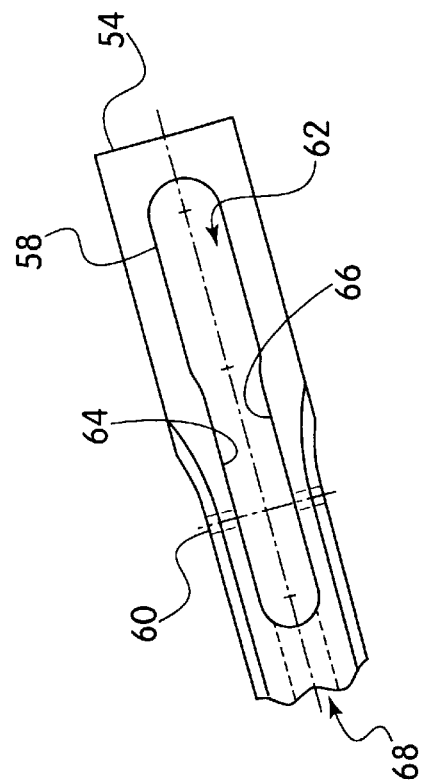
FIG. 8 shows a detail partial bottom view of the closed end of the outer shaft.
Figure 16:
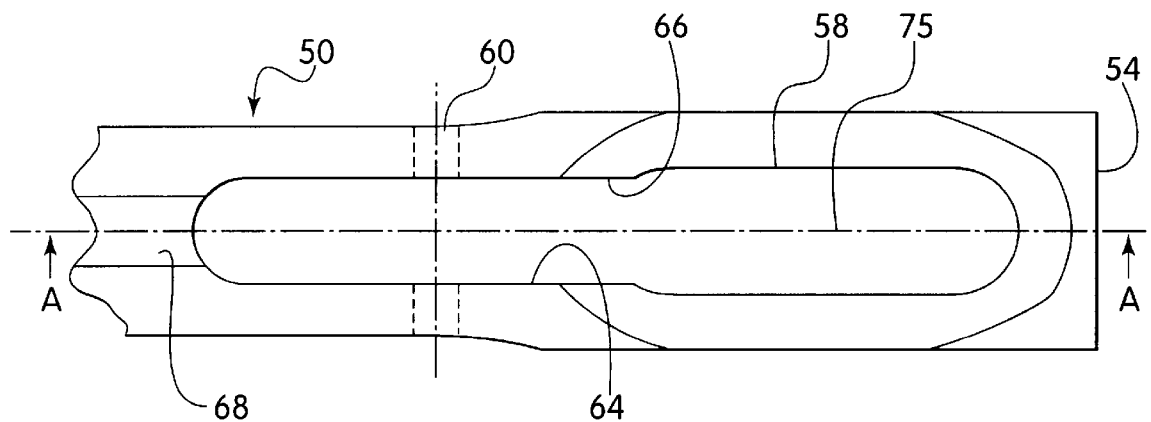
FIG. 16 shows a top detail partial view of the closed end of the outer shaft.

The inner tip 100 rotates relative to the outer shaft 50 around the tip axle 56, FIG. 2. The tip axle 56 is inserted through the axle hole 60 of the outer shaft 50, FIG. 6, and the tip hole 106 of the inner tip 100, FIG. 8. An actuator axle 44, FIGS. 2,3, can be used to restrain the actuator bar 176, to movement in one dimension. The actuator axle 44 is inserted through both sides of the outer shaft 50 through shaft hole 42 and through a slot 170, FIG. 12. The rotation of the inner tip 100 is achieved through the translation of the actuator bar 176 relative to the outer shaft 50 within a trough-like opening 68, FIG. 16.

The actuator bar 176 receives translational motion from the rotational movement of the actuator lever 46 relative to the hand grip 48 FIG. 1, or other means for translating the actuator bar 176. The actuator bar 176 engages the inner tip 100 with the tip end 178 via a radial ridge 182 having an upper surface 184 and a lower surface 186 which is wider than the upper surface 184, FIGS. 13 & 15. A preferred embodiment has a ratio of the surface area of the upper surface 184 to the surface area of the lower surface 186 of less than one. The lower surface 186 has a maximum dimension corresponding to the width of the actuator bar 176. In other words, in a preferred embodiment, the width of the lower surface 186 is equal to or less than the width of the actuator bar 176.

Figure 9:
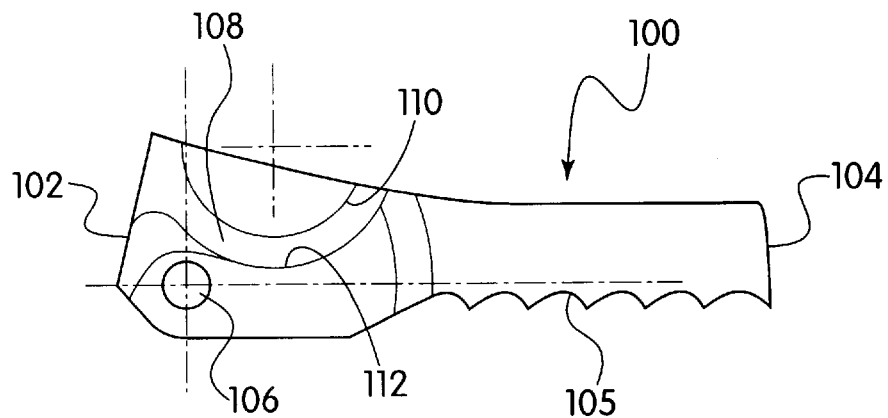
FIG. 9 shows a detail side view of the inner tip.
Figure 10:
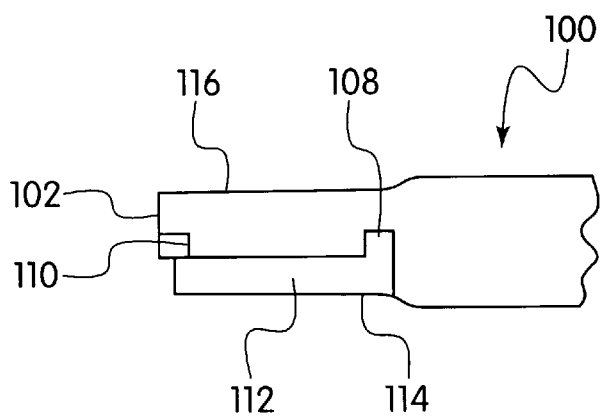
FIG. 10 shows a detail partial top view of the connected end of the inner tip.
Figure 11:
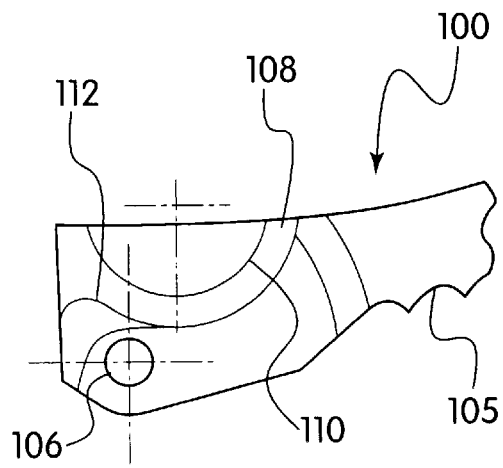
FIG. 11 shows a detail partial side view of the inner tip.
Figure 12:
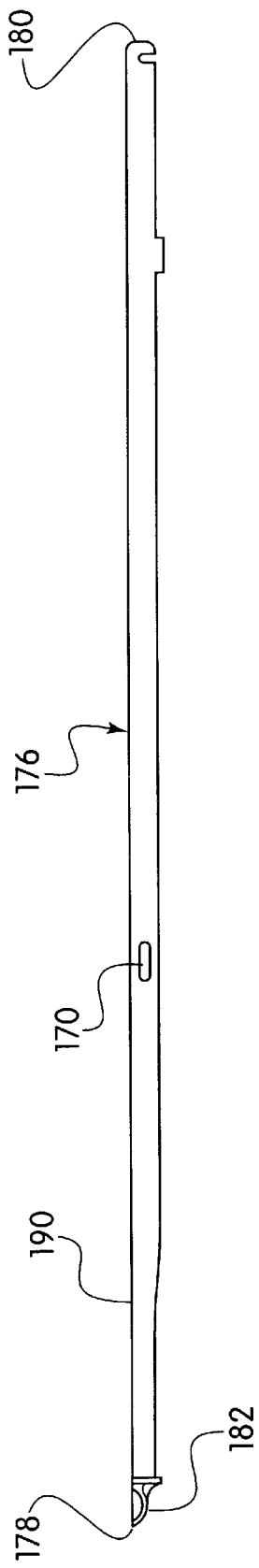
FIG. 12 shows a side view of the actuator bar.
Figure 15:
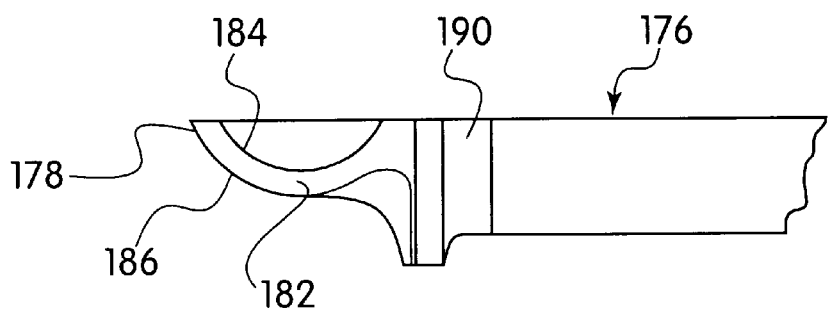
FIG. 15 shows a detail partial side view of the tip end of the actuator bar.

The radial ridge 182 of the actuation bar 176, FIG. 15, engages the inner tip 100 curved slot 108, FIGS. 9,10 which has a first surface 110 corresponding in size to the upper surface 184 and a second surface 112 corresponding in size to the lower surface 186, FIGS. 9,10,12. The ratio of the first surface 110 area to the second surface 112 area in a preferred embodiment is less than one. When the actuator end 180 moves away from the outer shaft 50, the upper surface 184 engages the first surface 110, causing the inner tip 100 to rotate around tip axle 56 to the open position 95. When the actuator end 180 moves towards the outer shaft 50, the lower surface 186 engages the second surface 112, causing the inner tip 100 to rotate around tip axle 56 to the closed position 96.

This arrangement provides a maximum surface area and therefore less stress between the inner tip 100 and the actuator bar 176 when the instrument 25 is moved from the open position 95 to the closed position 96, FIGS. 1, 2. The actuation of the actuator bar 176 is performed on the actuation end 180 by any actuation means commonly known in the art of which the hand grip 48 is but one embodiment. Other methods for providing translational movement to the actuator bar 176 could be utilized.

Figure 13:
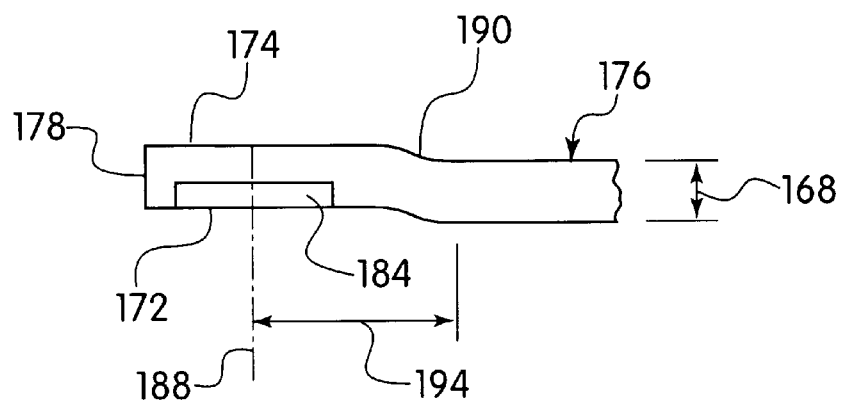
FIG. 13 shows a detail partial top view of the tip end of the actuator bar.
Figure 14:
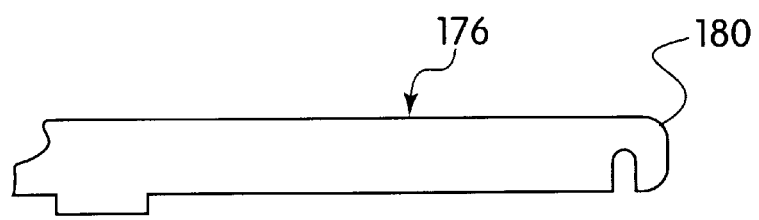
FIG. 14 shows a detail partial side view of the actuation end of the actuator bar.
Figure 17:
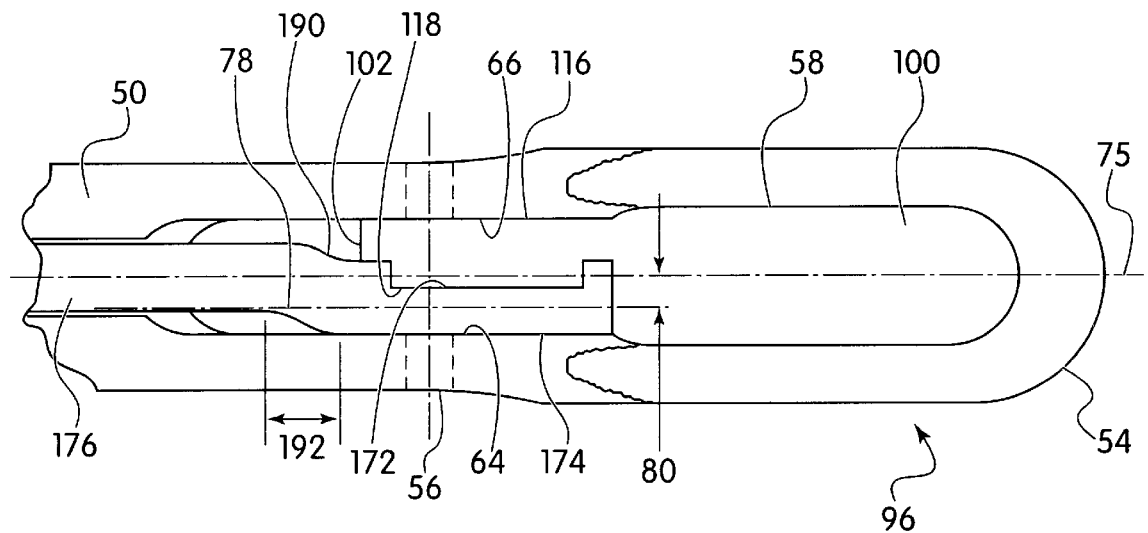
FIG. 17 shows a detail partial top view of the closed end of the outer shaft with the inner tip and actuator bar in the closed position.
Figure 18:
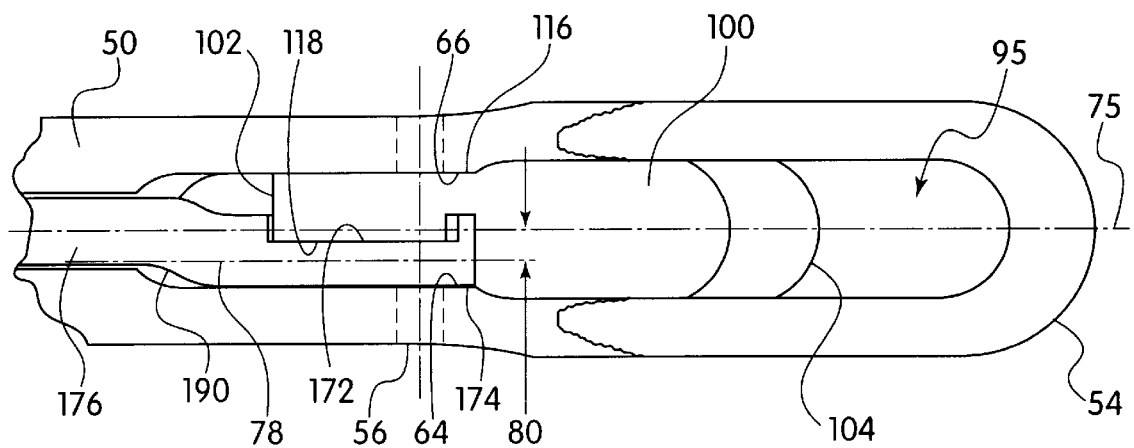
FIG. 18 shows a detail partial top view of the closed end of the outer shaft with the inner tip and actuator bar in the open position.

This larger surface area for the interface between the inner tip 100 and actuator bar 176 is further provided by the transition 190 of the actuator bar 176, FIGS. 13,17 & 18. The transition 190 can be described as a shifting of the longitudinal axis of the actuator bar 176 near the tip end 178. FIG. 17 shows a longitudinal axis 75 and an offset axis 78 where the offset axis 78 is shifted at a transition 190 a predetermined distance 80, FIG. 17. In a preferred embodiment, the offset axis 78 is shifted a distance in the range of 20%–75% of the width of the actuator. The shifting of the offset axis 78 occurs over a predetermined distance or shift distance 192. In a preferred embodiment, the shift distance 192 occurs over a maximum distance of two times the width 168 of the actuator bar 176. FIG. 13 shows a center 188 of the upper surface 184. Also shown is a transition location 194. This is the location on the length of the actuator bar 176 where the transition 190 occurs. In a preferred embodiment, the transition location 194 occurs within a maximum of four times the width 168 of the actuator bar 176 from the center 188. While this particular embodiment shows radii in the actuator bar 176 affecting the offset axis 78, other configurations could be utilized to shift the offset axis 78 such as linear transitions, steps and various sized radii.

The use of the transition 190 also allows the actuator bar 176 to maintain a constant width 168 along the entire length of the actuator bar 176. There is no necking down of the width 168 of the actuator bar 176 near the tip end 178.

The transition 190 allows the actuator bar 176 to engage the inner tip 100 in an offset position, this allows a greater potential contact surface interface between the actuator bar 176 and the inner tip 100. This results in larger surface areas of the second surface 112 and the lower surface 186, then could be provided if the actuator bar 176 had no transition 190. The larger surface areas of second surface 112 and lower surface 186 is especially important. Much of the prior art utilizes a connection between a straight actuator which necks down in height and width at the biting tip. The art is limited in the contact surface area that is possible between the components, because the actuator fits within the width of the biting tip.

In addition, the transition 190 allows the radial ridge 182 to engage the curved slot 108 of the inner tip 100 from the open side 114. This is a significant advantage in that the curved slot 108 with first surface 110 and second surface 112 can be machined from the open side 114 of the inner tip 100. The machining of curved slot 108 from the open side 114 provides an increased cost savings over machining from the connected end 102 as is done in the prior art. The access from the open side 114 decreases the complexity of cutting the curved slot 108. The nature of the relative openness of the curved slot 108 engagement with the radial ridge 182 makes access for cleaning the instrument 25 easier and safer in that it is easier to brush and penetrate the interface of the actuator bar 176 and the inner tip 100. The access to the open side 114 is greater than the prior art because the curved slot 108 is machined from the side as opposed to the connected end 102.

When the actuator bar 176 engages the inner tip 100 to move from the open position 95 to the closed position 96, this is when the highest force on these components is encountered. In moving from the open position 95 to the closed position 96 the tissue (not shown) that is required to be removed or grasped is between the inner tip 100 biting edge 105 and the outer shaft 50 die edge 58. The highest forces and therefor the highest stresses on the instrument occur at this time and this is when the instrument is most likely to fail, while a piece of very hard tissue is being lacerated or grasped for removal.

Figure 7:
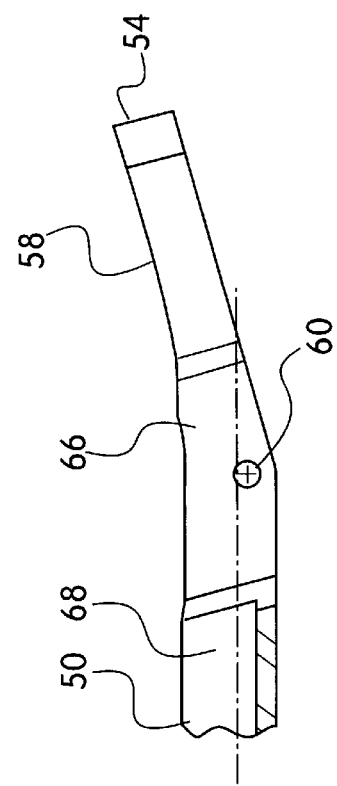
FIG. 7 shows a detail partial cross section view along longitudinal axis A—A in FIG. 16, of the closed end of the outer shaft.

Because there is an open side 114 on the tip 100, when the actuator bar 176 is contained within the outer shaft 50 and engaged with the inner tip 100, the actuator bar 176 tip end 178 flat side 174 is adjacent the tip opening 62 actuator edge 64, FIG. 7. While the inner tip 100 first side 116 is adjacent the tip edge 66 and the second side 118 is adjacent the depressed side 172 of the tip end 178, FIG. 13.

The interaction of the actuator bar 176, inner tip 100 and tip opening 62 results in three pair of contact surfaces between the components. In other words, frictional losses occur between flat side 174 and actuator edge 64, first side 116 and tip edge 66, and second side 118 and depressed side 172, best shown FIG. 17. These three pair of contact surfaces are a reduction as compared to the prior art which generally has 4 pair of contact surfaces.

A reduction in contact surfaces results in less potential friction from the operation of the components due to rough surfaces and tolerance build up and also less wear. This reduction in frictional losses means more of the force applied to the instrument 25 is available for lacerating or grasping action between the biting edge 105 and die edge 58. The instrument 25 is subject to less stress for the same amount of actuation and therefore there is less probability of failure or premature wearing.

To summarize, the transition 190 of the actuator bar 176 allows greater contact areas between the components, decreases the cost of machining, increases the accuracy of the machining such that a smoother action of the components occurs, decreases the number of contact surfaces between the components to three as opposed to the four found in the prior art decreasing the likelihood of hidden contaminants and promotes cleaning of the interface between the components.

Operation

Assuming the instrument 25 begins in the closed position 96, the operator engages the hand grip 48 and rotates the actuator lever 46 away from the hand grip 48. This rotational movement results in a translation of the actuator bar 176 towards the hand grip 48. The inner tip 100 connected end 102 is engaged with the tip end 178 and translation of the actuator bar 176 causes the inner tip 100 to rotate around a tip axle 56 which interconnects the inner tip 100 and outer shaft 50. The inner tip 100 opens to a position between the closed position 96 and the open position 95, FIGS. 1 & 2.

The interconnection between the inner tip 100 and the actuator bar 176 occurs between the first surface 100 of curved slot 108 and the upper surface 184 of radial ridge 182.

When the user desires to return the surgical tool 27 to the closed position 96, the actuator lever 46 is rotated towards the hand grip 48 reversing the translation of the actuator bar 176.

The lower surface 186 of the radial ridge 182 engages the second surface 112 of curved slot 108 causing inner tip 100 to rotate about tip axle 56 relative to the outer shaft 50. The biting edge 105 can then grasp or lacerate tissue or another object between the biting edge 105 and die edge 58.

Alternative Embodiment

Figure 19:
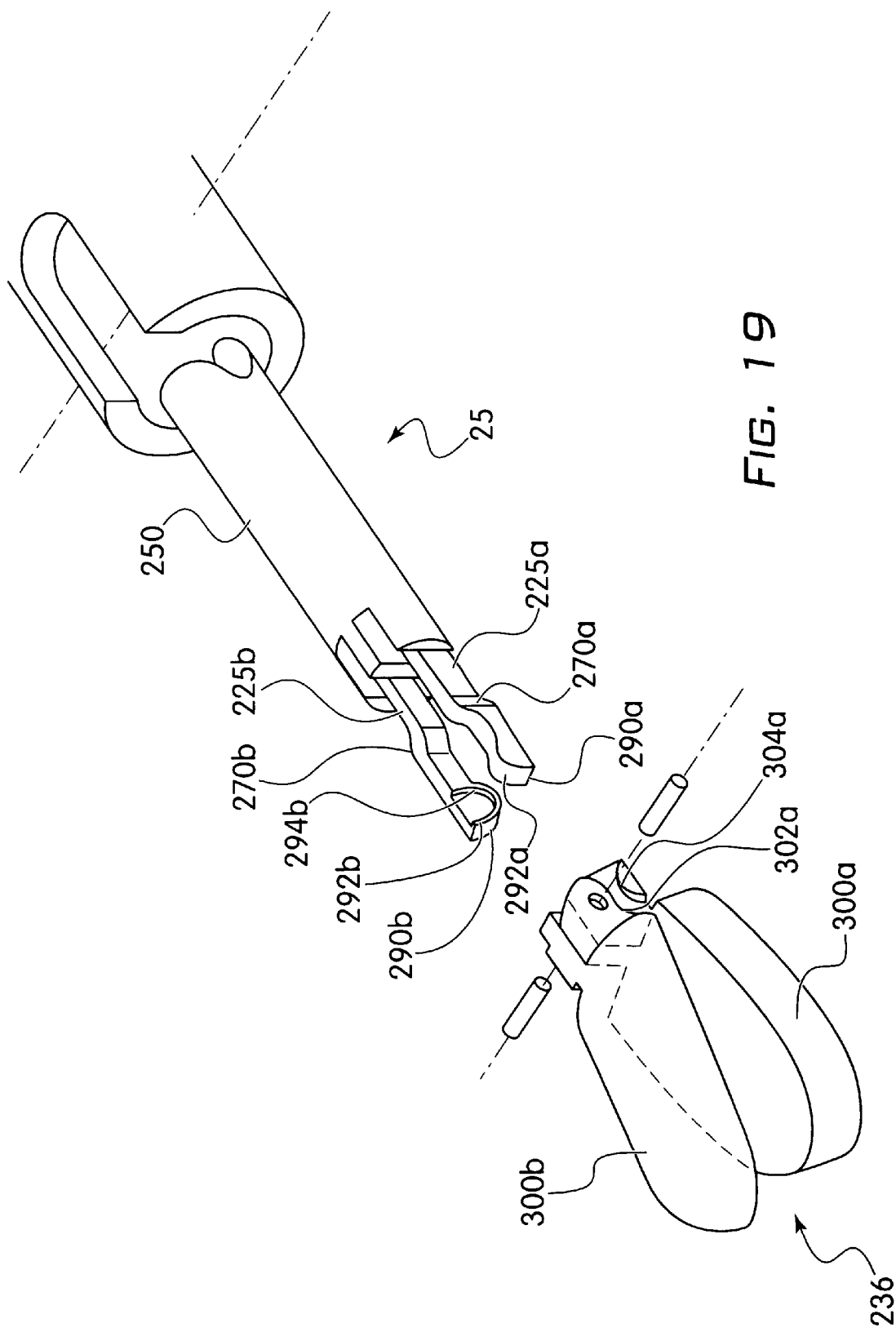
FIG. 19 shows an exploded partial view of an alternative embodiment of an instrument utilizing two cuppers working in conjunction with two actuator bars.
Figure 20:
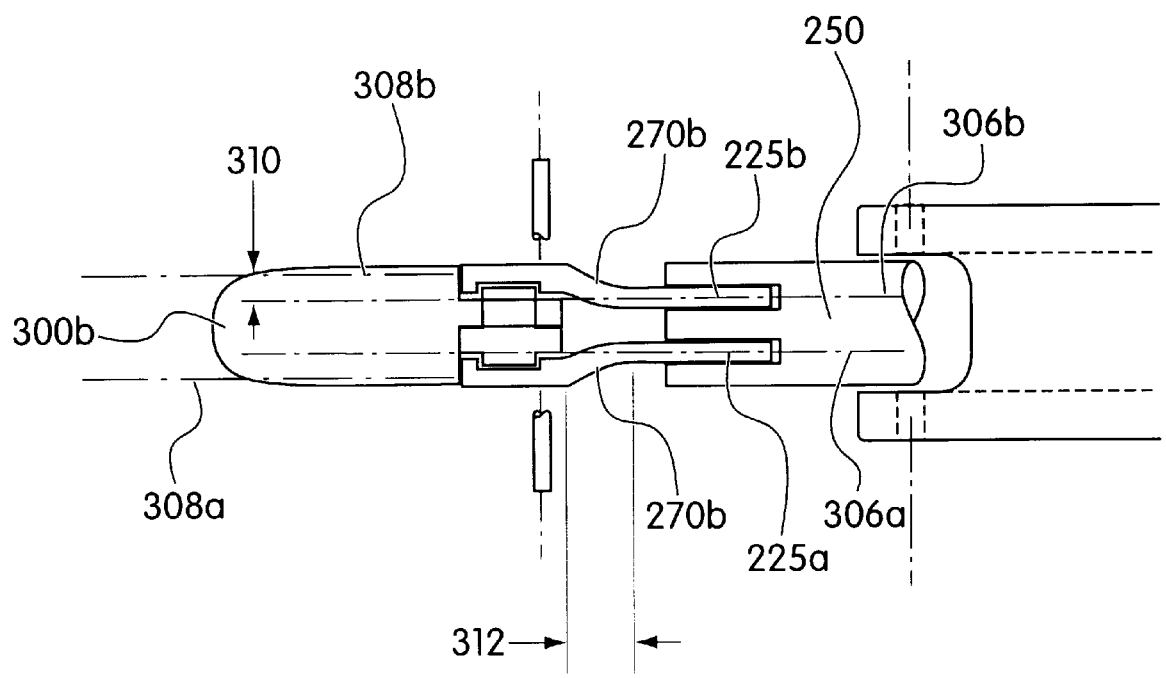
FIG. 20 shows a detail partial assembled top view of the dual actuator embodiment of FIG. 19.

FIGS. 19 and 20 show an alternative embodiment of an instrument 25. This embodiment has two actuator bars 225a, 225b which are mirror images of one another contained within a retainer 250. The actuator bars 225a, 225b also have transitions 270a, 270b with second ends 290a, 290b for engagement with cuppers 300a, 300b for grasping, lacerating or cupping another object. While this embodiment and the one described prior, generally show the transitions and offset axis in a single plane generally horizontal, other offset directions could be utilized. This may be particularly useful in the embodiment shown in FIGS. 19 & 20. In this embodiment, the direction of the offset axis could be vertical either above or below the longitudinal axis, thereby providing for some mechanical advantage to, for example, the cuppers 300a, 300b.

FIG. 20 shows the actuator bars 225a,b having a longitudinal axis 306a,b with transitions 270a,b resulting in offset axis 308a,b where the offset axis 308a,b are offset a distance 310 over a shift distance 312. The distance 310 is in the range of 20%–70% of the width of the actuator bar 225a,b while the length or shift distance 312 over which this occurs is a maximum of two times the width of the actuator bar 225a,b.

The second ends 290a, 290b have push surfaces 292a, 292b for engagement with cuppers 300a, 300b first surfaces 302a, 302b (not shown) for biasing the cuppers 300a, 300b to the closed position 235, (not shown)

The second end 290a, 290b also have pull surfaces 294a (not shown), 290b for engagement with second surface 304a, 304b (not shown) to bias the cuppers 300a, 300b to an open configuration, FIG. 19.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

We claim:

1. A tool for lacerating or grasping other objects, the tool comprising:
    an outer shaft with an open end and a closed end and an opening located parallel to a longitudinal axis extending from the open end to near the closed end;
    an actuator bar with a tip end and an actuation end and a constant width, a transition near the tip end resulting in the tip end having a longitudinal offset axis displaced horizontally from the longitudinal axis in a single plane, the actuation end engaging a translation means for translation of the actuator bar relative to the outer shaft, a single radial ridge located near the tip end for engagement with an inner tip; and
    the inner tip rotabonally engaged to the outer shaft near the closed end and the inner tip having a connected end, the inner tip interengaging the radial ridge with a sinule curved slot located on an open side where translation of the actuator bar relative to the outer shaft results in rotation of the inner tip relative to the outer shaft.

2. The tool of claim 1, wherein:
    the translation means is a hand grip.

3. The tool of claim 1, further comprising:
    the outer shaft having a die edge near the closed end and the inner tip having a biting edge, the die edge and biting edge for interacting with objects locatable between the biting edge and the die edge.

4. The tool of claim 1, further comprising:
    the radial ridge having an upper surface smaller in width than a lower surface and the curved slot having a first surface smaller in width than a second surface.

5. A tool for interacting with objects, the tool comprising:
    an outer shaft with an open end and a closed end and a trough-like opening located parallel to a longitudinal axis extending from the open end to near the closed end, a shaft hole and an axle hole located perpendicular to the longitudinal axis through the outer shaft;
    an actuator bar with a tip end and an actuation end with a slot located therebetween and the actuator bar having a constant width, a transition near the tip end resulting in the tip end having a longitudinal offset axis displaced horizontally from the longitudinal axis in a single plane, the actuation end engaging a translation means for translation of the actuator bar relative to the outer shaft, a single radial ridge located near the tip end for engagement with an inner tip; and
    the inner tip rotatably attached to the outer shaft near the closed end by a tip axle through the axle hole, the inner tip having a connected end, the inner tip interengaging the radial ridge with a single curved slot located on an open side such that translation of the actuator bar relative to the outer shaft results in rotation of the inner tip relative to the outer shaft.

6. The tool of claim 5, further comprising:
    the radial ridge having an upper surface smaller in width than a lower surface and the curved slot having a first surface smaller in width than a second surface.

7. The tool of claim 5, wherein:
    the translation means is a hand grip.

8. The tool of claim 5, further comprising:
    the outer shaft having a die edge near the closed end and the inner tip having a biting edge, the die edge and biting edge for interacting with objects locatable between the biting edge and the die edge.

9. A tool for interacting with objects, the tool comprising:
    an outer shaft with an open end, a closed end and a trough-like opening located parallel to a longitudinal axis extending from the open end to near the closed end, a shaft hole and an axle hole located perpendicular to the longitudinal axis through the outer shaft, a die edge circumscribing a tp opening near the closed end for interacting with an inner tip;
    an actuator bar with a tip end and an actuation end having a slot perpendicular to a longitudinal axis there between, the actuator bar having a constant width, a
    transition near the tip end resulting in the tip end having a longitudinal offset axis displaced horizontally from the longitudinal axis in a single plane, the actuation end engaging a translation means for translation of the actuator bar relative to the outer shaft in a direction parallel to the longitudinal axis, a single radial ridge located near the tip end for engagement with the inner tip; and
    the inner tip rotatably attached to the outer shaft near the closed end by a tip axle through the axle hole, the inner tip locatable within a tip opening in a closed position, the inner Up having a connected end opposite a biting end, the inner tip interengaging the radial ridge with a single curved slot located on an open side such that translation of the actuator bar relative to the outer shaft results in rotation of the inner tip relative to the outer shaft.

10. The tool of claim 9, further comprising:
    the radial ridge having an upper surface smaller in width than a lower surface and the curved slot having a first surface smaller in width than a second surface.

11. The tool of claim 9, wherein:
    the translation means is a hand grip.

12. The tool of claim 9, further comprising:
    the outer shaft having the die edge near the closed end and the inner tip having the biting edge, the die edge and the biting edge for interacting with objects locatable between the biting edge and the die edge.

* * * * *